United States Patent [19]

Cohen et al.

[11] 4,421,393

[45] Dec. 20, 1983

[54] VISUAL FIELD PERIMETER AND PSYCHOMOTOR TRACKING PERFORMANCE MEASURING APPARATUS

[75] Inventors: Malcolm M. Cohen; James J. Palumbo, both of Philadelphia; David C. Johanson, Warminster; John G. Nelson, Newtown, all of Pa.

[73] Assignee: The United States of America as represented by the Secretary of the Navy, Washington, D.C.

[21] Appl. No.: 257,683

[22] Filed: Apr. 27, 1981

[51] Int. Cl.³ .............................................. A61B 3/02
[52] U.S. Cl. ................................................. 351/224
[58] Field of Search .............................. 351/224–226

[56] References Cited

U.S. PATENT DOCUMENTS

| | | |
|---|---|---|
| 1,601,394 | 9/1926 | Hunsicker . |
| 1,802,997 | 4/1931 | Yetta . |
| 2,744,441 | 5/1956 | Cox . |
| 2,803,990 | 8/1957 | MacKnight . |
| 3,025,755 | 3/1962 | Koetting . |
| 3,482,905 | 12/1969 | Ben-Tovim . |
| 3,718,386 | 2/1973 | Lynn et al. . |
| 4,059,348 | 11/1977 | Jernigan . |
| 4,063,807 | 12/1977 | Gelius et al. . |

OTHER PUBLICATIONS

*Aviation Space and Environmental Medicine,* vol. 48, No. 2, Feb. 1977, p. 91, Gillingham, K. K. et al., "Visual Field Contraction During G Stress at 13°, 45°, and 65° Seatback Angles".

*Primary Examiner*—John K. Corbin
*Assistant Examiner*—Rodney B. Bovernick
*Attorney, Agent, or Firm*—R. S. Sciascia; Henry Hansen

[57] ABSTRACT

A system for evaluating tolerance to high acceleration as a function of visual field perimeter and psychomotor tracking ability. A semicircular array of light-emitting diodes (LED's) subtend the lateral field of view of a subject. Pairs of opposed LED's are sequentially illuminated inwardly or outwardly at a programmed rate. A control stick manipulated by the subject provides a nulling signal for maintaining a desired pair of LED's illuminated.

8 Claims, 5 Drawing Figures

VISUAL FIELD PERIMETER AND PSYCHOMOTOR TRACKING PERFORMANCE MEASURING APPARATUS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to apparatus for simultaneously measuring the visual field perimeter and psychomotor tracking performance of a human subject, and more particularly to apparatus for measuring human tolerance as a function of visual field perimetry and psychomotor tracking performance at different levels of acceleration (G).

When a human subject is exposed to high vertical upward or "eyeballs down" acceleration ($G_z$), blood supply to the eyes and brain is reduced due to increased loading of the heart-brain hemodynamic column. Progressive reduction of blood flow results in a dimming of vision or "gray-out", a narrowing of the visual field, a total loss of vision or "black-out", and ultimately a loss of consciousness. Because intraocular pressures exceed intracranial pressures, blood flow to the eyes is interrupted before blood flow to the brain, and loss of vision generally precedes loss of consciousness. In addition to the hemodynamic effects, exposure to increased $G_z$-forces degrades psychomotor tracking performance. By measuring the extent and rate of narrowing of the visual field perimeter and the psychomotor tracking ability of a subject, it is possible to establish an end point for tolerance to $G_z$-forces.

Prior art devices have been found unsuitable for this particular purpose. In general, the response parameters used for determining acceleration tolerance are not related to the natural and instinctive movements of the subject. They require extensive training and physical endurance. Most devices also use white incandescent lamps generating light in a spectral range which is too easily detected by the retinal receptors (rods), and which is transiently visible after the lamps have been deenergized. One device assesses G-tolerance with a linear array of white lights spaced along an arcuate bar subtending a viewing angle on each side of a central red light. Opposite lights are electrically connected in pairs and sequentially illuminated inwardly or outwardly at a fixed rate. The direction is reversed by operation of a hand-operated push button. The G-tolerance of the subject is assessed by his ability to maintain the light pairs illuminated near the edge of his useful vision. This system is susceptible to "cheating" because a skillful subject could deceptively operate the push button at a rate which would maintain a constant light position, even though his peripheral vision has been reduced to where the light is not visible. In addition, this device cannot measure psychomotor tracking performance because the rate at which the illumination moves in or out remains constant.

Another system involves a lamp randomly illuminated and located in the subject's visual periphery. When the lamp is illuminated, the subject immediately presses a button to extinguish it. If he does not respond within a few seconds, the subject is considered not to have seen the lamp, and his vision is regarded as impaired. The limits of the subject's visual field and the rate at which it collapses are not measured. In addition, there is no measure of visual functioning except at the discrete points in time when the lamp is illuminated, and no indication of psychomotor tracking ability.

SUMMARY OF THE INVENTION

Accordingly, it is an object of the present invention to provide apparatus for the combined and simultaneous measurement of visual field perimetry and psychomotor tracking ability of a human subject. Another object is to provide a system for evaluating human tolerance to various acceleration levels as a function of a subject's visual field perimetry and psychomotor tracking ability. Still another object is to provide apparatus for indicating visual functioning from the time-averaged mean position of the visual field perimeter, and psychomotor tracking performance from the transfer function relating programmed input driving signals to manual control output signals. A further object of the invention is to provide a visual field measuring device which operates in the chromatic region where the threshold for peripheral vision is high and therefore relatively more sensitive to changes in efficiency of the retinal receptors (rods). Another object is to provide apparatus in which graded force control of the position of illuminated pairs of lights for continuous tracking can be achieved by a subject with relatively little training, and which can be programmed with variable and constant signals for precluding the possibility of "cheating". Still a further object is to provide apparatus which utilizes simplified digital logic and integrated circuits for driving and processing signals.

Briefly, these and other objects of the invention are accomplished by apparatus for assessing human tolerance to various acceleration levels as a function of a subject's visual field perimeter and psychomotor tracking ability. An arcuate array of light-emitting diodes (LED's) are displayed in the lateral field of view of a subject. A programmed signal generator sequentially illuminates pairs of opposed light emitting diodes inwardly or outwardly at a programmed rate. A force control stick, manipulated by the subject, provides a nulling signal for maintaining any visible pair of LED's illuminated, and thereby provides indicia of his maximum field of view and of his psychomotor tracking ability.

For a better understanding of these and other objects and aspects of the invention, reference may be made to the following detailed description taken in conjunction with the accompanying drawings wherein:

DESCRIPTION OF THE PREFERRED EMBODIMENT

Figure 1:
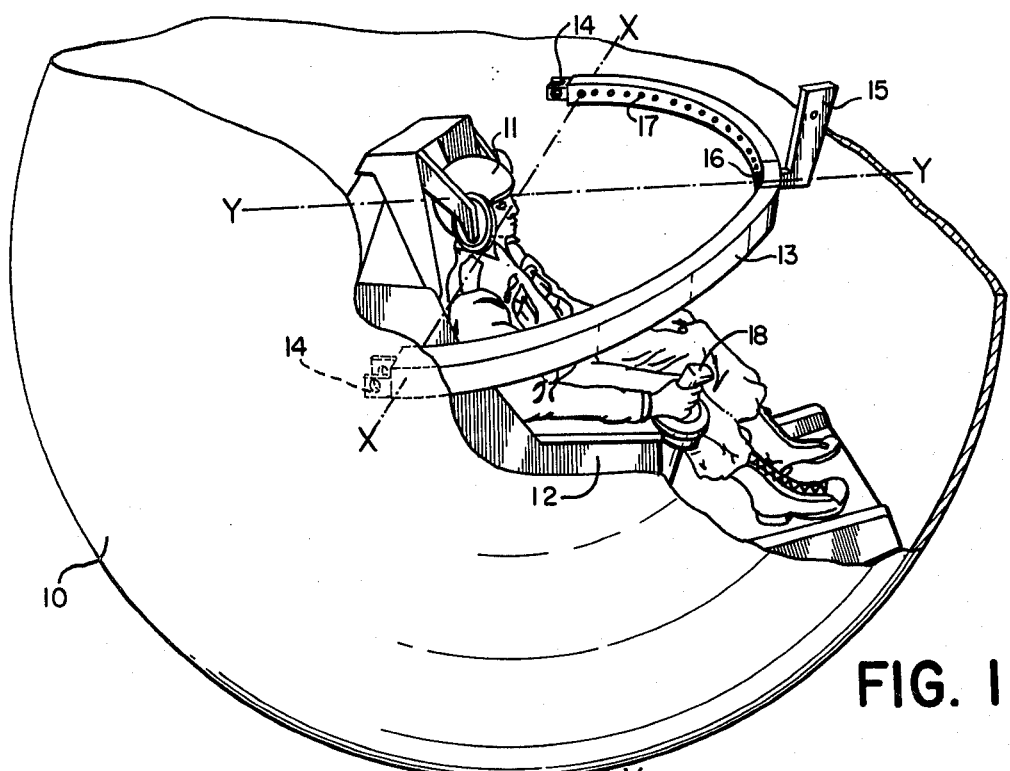
FIG. 1 is a perspective view of visual field perimeter and psychomotor tracking performance measuring apparatus according to the invention as applied in the gondola of a human centrifuge.

Referring now to the drawings wherein like characters designate like or corresponding parts throughout the several views, FIG. 1 illustrates an aircrewman or subject seated in a spherical gondola 10 with his head secured in a helmet 11 rigidly fixed to the back of seat 12 to prevent side-to-side head movement. A semicircular light bar 13, preferably of aluminum channel, is mounted within the gondola at pins 14 and post 15 in a plane defined by a transverse axis X—X passing through the eyes and a forward axis Y—Y orthogonal thereto.

Figure 2:
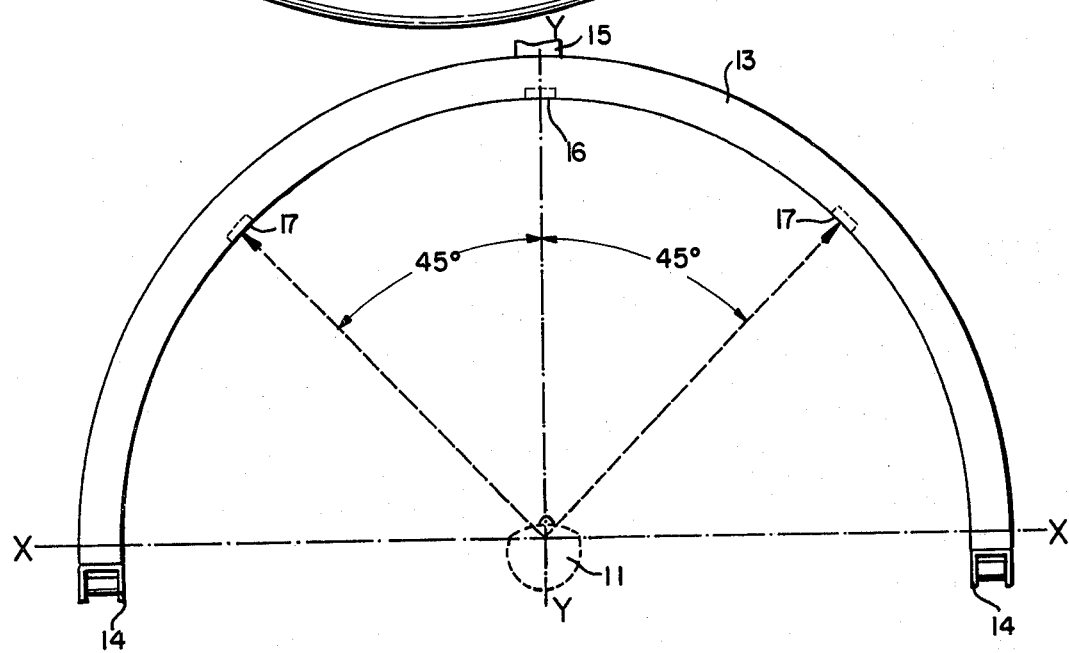
FIG. 2 is a plan view of an arcuate light bar of the apparatus of FIG. 1.

As shown in FIG. 2, bar 13 subtends a 90° viewing angle on either side of axis Y—Y and includes 120 red light-emitting diodes (LED's) 17 located every $1\frac{1}{2}°$ around the inner circumference with the outer or 90°-LED's 17 at the X—X axis. At the center or 0° position at the Y—Y axis is a continuously illuminated white incandescent lamp 16. LED's 17 at corresponding angles on either side of lamp 16 are electrically connected in parallel so that each pair can be illuminated independently of the others.

Figure 4:
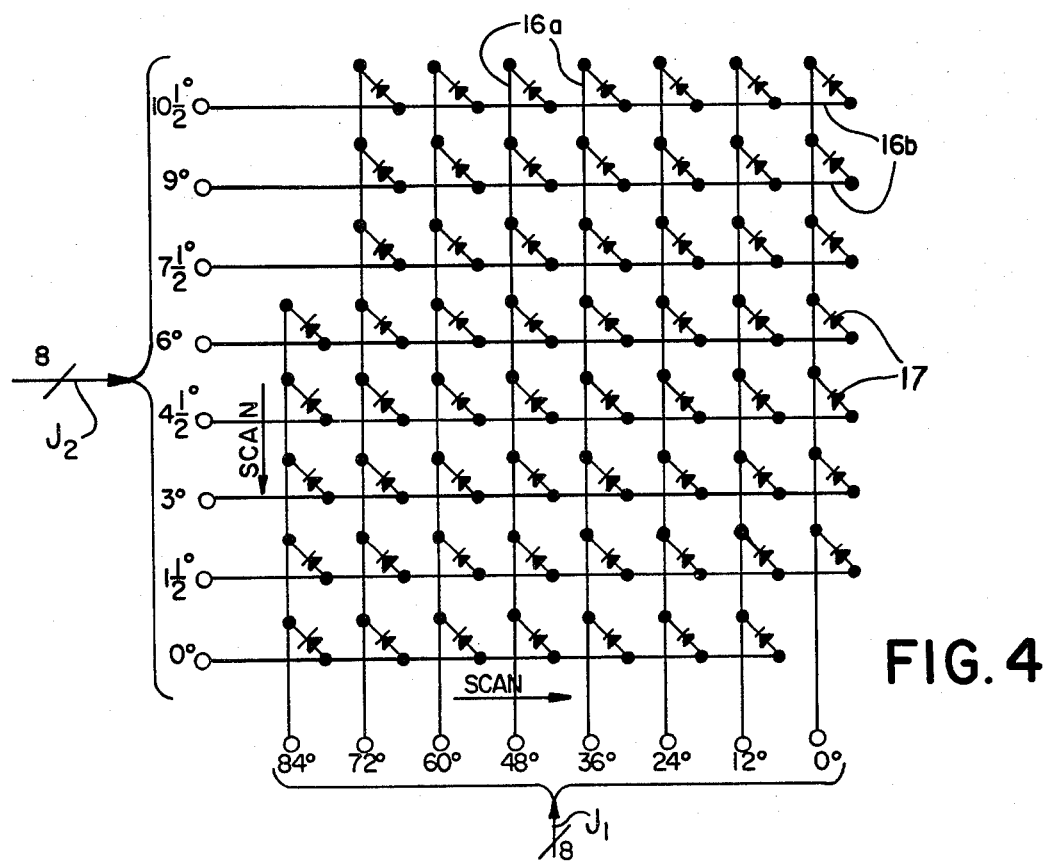
FIG. 4 diagrammatically illustrates an electrical circuit for energizing respective diodes in the light bar of FIG. 2.

FIG. 4 illustrates the manner in which the LED pairs are electrically energized. The LED symbols in the matrix represent pairs of opposed LED's connected across two conductors, each conductor being selected from separate sets of eight conductors 16a and 16b respectively within bar 13. By energizing one conductor of each set, a single LED pair is energized. For example, energizing the 36°-conductor of set 16a and the 9°-conductor of set 16b, the LED pair located at the 45° viewing angle is illuminated.

A force control stick 18 mounted on seat 12 and manipulated by the subject during a test run provides a signal for controlling illumination of diodes 17.

Figure 3:
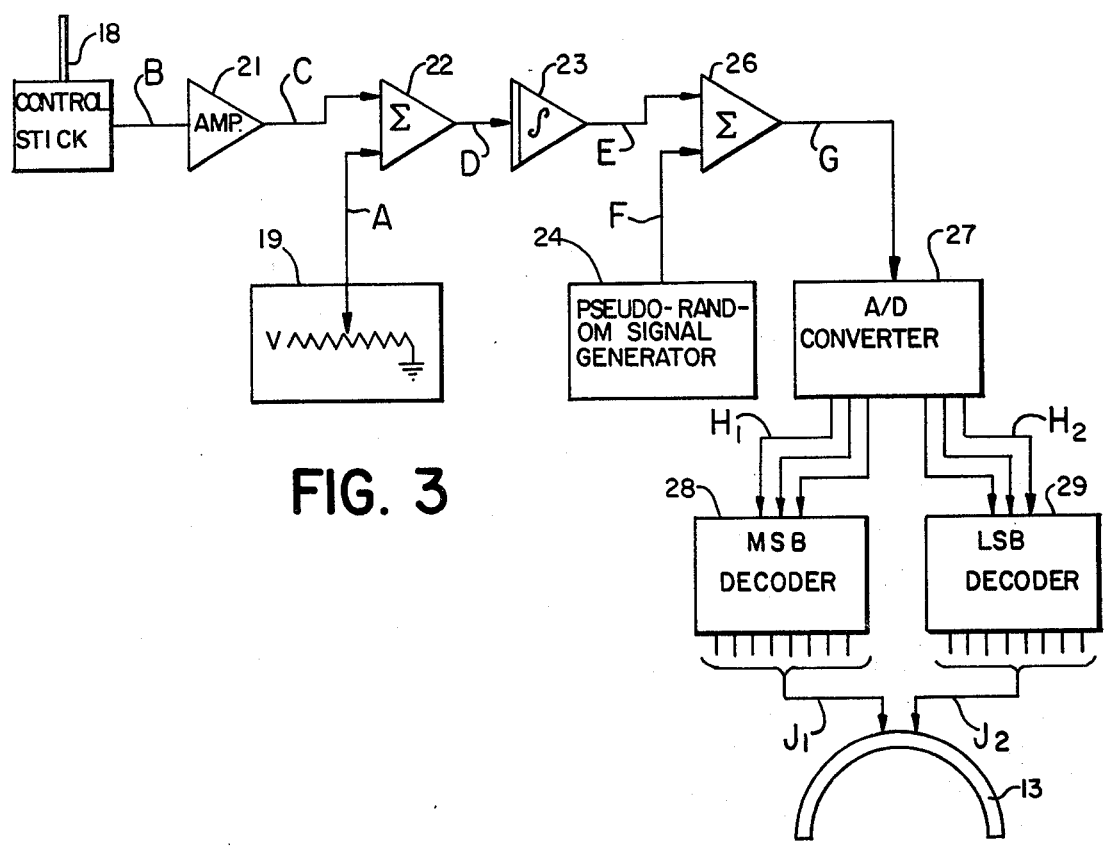
FIG. 3 is a block diagram of an electrical control system utilized in the apparatus of FIG. 1.

Referring now to the block diagram of FIG. 3, a fixed DC voltage signal A is manually selected at a voltage divider 19 for determining a constant rate, between 0° and 150° per second, at which the LED's 17 are sequentially illuminated toward the 0°-lamp. Once established for a test run, it may be modified by the subject manipulating the force control stick 18 to generate a bipolar voltage signal B at its output proportional to the applied force. Signal B is applied to a scaling amplifier 21, the gain of which adjusts the sensitivity of stick 18 relative to the rate signal A. The scaled voltage output C of amplifier 21 is then summed in a summing amplifier 22 with signal A resulting in a rate offset signal D to an integrator 23. Signal D is then integrated with a fixed time constant to effectively change it from a rate control voltage to a position control voltage. With a constant rate signal A, the level of signal E will vary at a rate proportional to the magnitude of the force applied to stick 18. In the absence of a force applied to stick 18, there is no signal B and the rate offset signal D causes the output of integrator 23 output E to increase as a ramp function.

A pre-programmed, position voltage signal F is provided by a pseudo-random signal generator 24 for preventing a subject from anticipating or conditioning his force response on control stick 18 regardless of his visual perception or psychomotor tracking ability. Signals F and E are combined in a summing amplifier 26, and the analog output position signal G is applied to the input of a 6-bit analog-to-digital converter 27 which successively approximates signal G in a 6-bit binary form. The decimal equivalent of each code corresponds to a separate pair of LED's 17 with "1" corresponding to the 90°-LED's, "2" corresponding to the $88\frac{1}{2}°$-LED's, and so on up to "60" which corresponds to the $1\frac{1}{2}°$-LED's.

The 6-bit binary signal from converter 27 is split into two signals $H_1$ and $H_2$ of three bits each. Signal $H_1$ is composed of the three most significant bits (MSB's), and $H_2$ of the three least significant bits (LSB's), and are decoded into one of eight outputs $J_1$ and $J_2$ by decoders 28 and 29 respectively. Outputs $J_1$ connect to conductor set 16a or the cathodes of LED's 17 and output $J_2$ to conductor set 16b or the anodes. With this arrangement, conductors 16b are scanned eight times as fast as conductors 16a when the illuminated LED pair are sequenced over their entire range. For example, signal $J_2$ will sequence down through $10\frac{1}{2}°$ to 0° while signal $J_1$ stays at 84°. This corresponds to sequentially illuminating the 90°- to 84°-LED's, there being no LED's in the matrix at $94\frac{1}{2}°$, 93° and $91\frac{1}{2}°$. Then signal $J_1$ will energize at 72° while signal $J_2$ sequences down from $10\frac{1}{2}°$ to 0°. This corresponds to illuminating the $82\frac{1}{2}°$- to 60°-diodes. With no force applied to control stick 18, the sequencing will continue until signals $J_1$ and $J_2$ are at 0° each where there is no LED.

Figure 5:
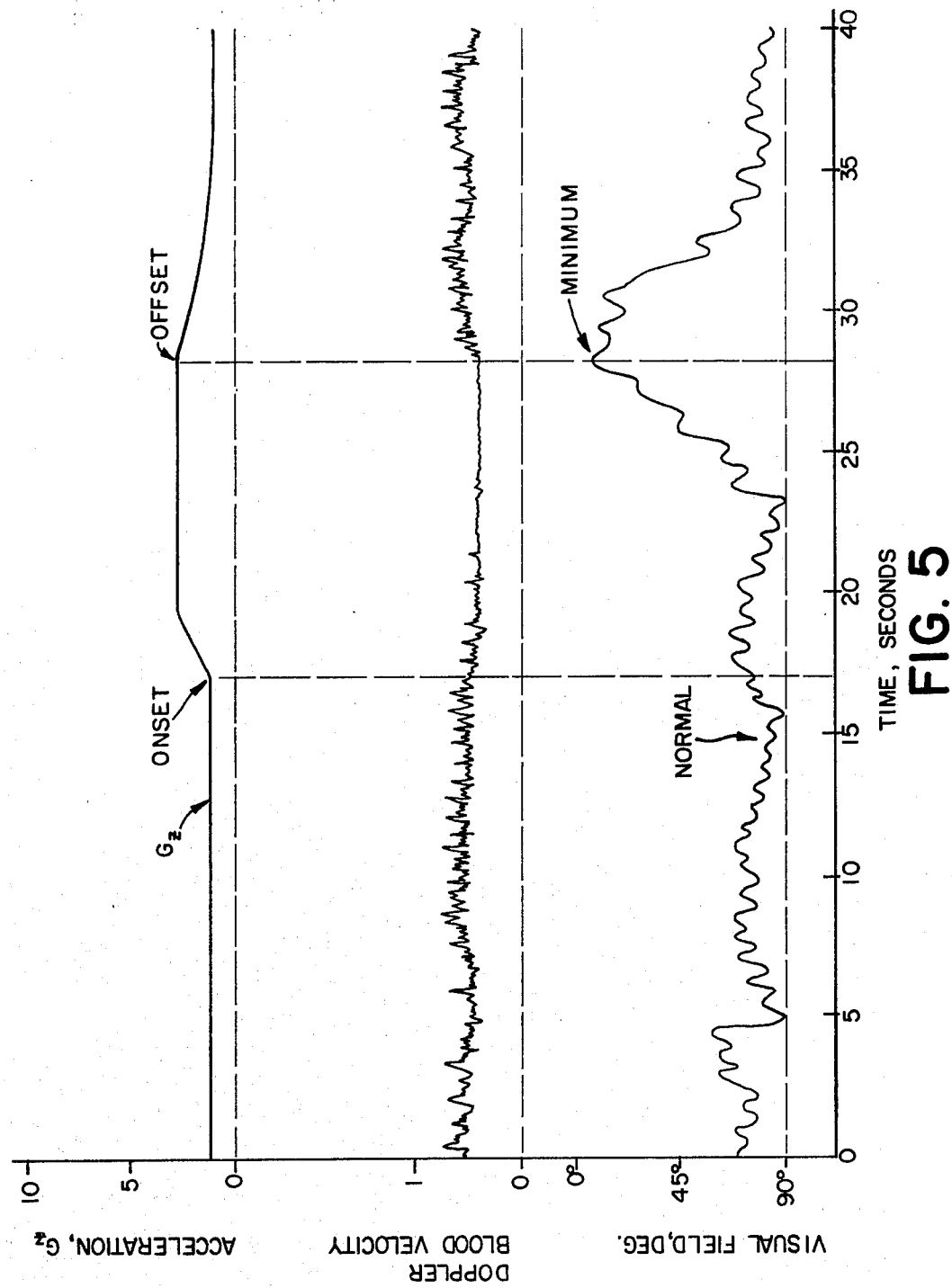
FIG. 5 is a typical graph representing the visual field perimeter and psychomotor tracking ability of a subject under a variable G-loading.

Operation of the invention is now summarized, with reference to a typical test run in which a subject is exposed over a 40-second period to the acceleration profile $G_z$ illustrated in the graph of FIG. 5. The voltage divider 19 is adjusted to provide a fixed DC voltage at signal A which is integrated into a ramp signal G to sequentially illuminate LED's 17 inwardly at a rate of 60° per second. For purpose of this test run, signal F from generator 24 is maintained at zero. The subject is maintained at 1 G for 17 seconds while he attempts to maintain the LED pairs illuminated at the perimeter of his visual field by increasing or decreasing the rate signal B with control stick 18. In FIG. 5, the doppler blood velocity graph shows the blood velocity at the temporal artery in normal pulsation and the visual field perimeter of the subject to be between 60° and 90°.

The acceleration is then increased to $2\frac{1}{2}$ G's. In about 5 seconds, the blood velocity decreases to near zero resulting in a significant drop in peripheral vision to about 15°. This is manifested by the subject's setting of the outer limits of illumination of the LED's to approximately 15° from straight forward (or a 30° visual field perimeter). As a safety feature against excessive acceleration, selected LED's, such as the pair at the 30° field perimeter, are interlocked with the human centrifuge to shut it off. At approximately 28 seconds, into the run, the acceleration is gradually reduced back to 1 G for the remainder of the run. It will be noted that the subject's blood velocity and peripheral vision returned to normal. By varying the signal F according to a pseudo-random program, illumination of the LED's at the periphery of his vision may be moved in or out. The subject's ability to follow the programmed changes will verify whether or not he can actually see LED's which he purports to control.

Some of the many advantages of the invention are now readily apparent. For example, combined and simultaneous measurement of the visual field perimetry and psychomotor tracking ability of a human subject is now possible. The system affords evaluation of human tolerance to various acceleration levels and provides an indication of visual functioning from the time-averaged to mean position of the visual field perimeter, and the psychomotor tracking performance from the transfer function relating program input driving signals to manual control output signals.

It will be understood that various changes in the details, steps and the arrangement of parts which have been hereby described and illustrated in order to explain the nature of the invention and may be made by those skilled in the art within the principle and scope of the invention as expressed in the appended claims.

What is claimed is:

1. Apparatus for simultaneously measuring a subject's visual field perimeter and psychomotor tracking ability, comprising, in combination:

first control means providing a first analog signal indicative of a preselected constant rate of change of the subject's angle of view;

second control means formed to be manipulated by the subject for providing a second analog signal indicative of the force applied thereto;

control means connected to recieve said first and second signals for providing a third digital signal indicative of the integrated sum of said first and second signals;

display means having a curved array of lights formed to subtend the subject's angle of view at equiangular positions about the angle bisector with opposed pairs of lights connected in parallel, and connected to receive said third signal for illuminating opposed pairs of said lights in response thereto.

2. Apparatus according to claim 1 wherein said control means further comprises:

first summing means connected to receive said first and second signals for providing a signal indicative of the sum of the received signals;

integrating means connected to receive said first summing means signal for producing a multibit binary-coded signal indicative of the integral of said summing means signal;

first decoder means connected to receive the most significant bits of said binary-coded signal for energizing one of a first plurality of outputs of said third signal; and second decoder means connected to receive the least significant bits of said binary-coded signal for energizing one of a second plurality of outputs of said third signal.

3. Apparatus according to claim 2 wherein said integrating means further comprises:

an integrator connected to receive said summing means signal for producing an analog signal indicative of the integration of the received signal;

generator means for producing a pseudo-random analog signal;

second summing means connected to receive the analog signals from said integrator and generator means for producing a signal indicative of the sum of the received analog signals; and converter means connected to receive said second summing means signal for producing the binary signal.

4. Apparatus according to claim 2 wherein each of said first plurality of outputs are connected in common to one terminal of a selected plurality of said light pairs and the other terminal of each of said commonly connected light pairs are connected to respective ones of said second plurality of outputs.

5. Apparatus according to claim 1 wherein said lights are diodes emitting light in the red spectrum.

6. Apparatus according to claim 5 wherein said display means further includes a white light at the angle bisector.

7. Apparatus according to claim 3 wherein said first control means comprises:

a voltage divider for providing a selected constant voltage output; and an amplifier connected to receive said voltage output for producing said first analog signal.

8. Apparatus according to claim 4 wherein said first plurality of outputs correspond to a like number of equi-angular cardinal positions in either bisected angle of view, and said second plurality of outputs correspond to a like number of equi-angular positions between said cardinal positions.

* * * * *